United States Patent [19]

Hiranuma

[11] Patent Number: 4,764,113
[45] Date of Patent: Aug. 16, 1988

[54] SEMI-ADJUSTABLE DENTAL ARTICULATOR
[75] Inventor: Kenji Hiranuma, Nagoya, Japan
[73] Assignee: Noboru Onuki, Japan
[21] Appl. No.: 887,994
[22] Filed: Jul. 18, 1986
[51] Int. Cl.[4] ............................................. A61C 11/00
[52] U.S. Cl. ...................................... 433/56; 433/58; 433/59
[58] Field of Search ........................ 433/53, 56, 58, 59

[56] References Cited

U.S. PATENT DOCUMENTS

| | | | |
|---|---|---|---|
| 2,235,524 | 3/1944 | Lentz | 433/58 |
| 3,159,915 | 12/1964 | Beu et al. | 433/56 |
| 3,160,955 | 12/1964 | De Pietro | 433/56 |

Primary Examiner—Robert Peshock
Attorney, Agent, or Firm—Toren, McGeady & Associates

[57] ABSTRACT

In order to allow positive and quick fixation as well as centric fixation of a condyle portion with a very simplified operation, a semi-adjustable dental articulator is of the construction that an adjusting-and-fixing knob of the adjustable guide plate for the condylar box is provided to protrude beyond the upper surface of the condylar box, and also that an orbita indicator is detachably, semi-fixedly and slidably mounted on the incisal guide pin. On a corner edge line between a back surface and an outer side surface of each of a pair of laterally spaced upright frame portions of an articulator body is provided with an indicator notch aligned with an occlusion plane in height and another indicator notch aligned with an ear in height.

5 Claims, 3 Drawing Sheets

SEMI-ADJUSTABLE DENTAL ARTICULATOR

BACKGROUND OF THE INVENTION (a) Field of the Invention

The present invention relates to a dental articulator, and more particularly it pertains to an improvement of the Arcon-type semi-adjustable dental articulator.

(b) Description of the Prior Art

An articulator is a simulation device of man's chin, and it has been devised for the purpose of making an artificial denture or the like outside man's chin. The Arcon-type semi-adjustable articulator refers to such an articulator as having the structure comprising a pair of condyle guides for the upper bow and also a pair of condyle balls for the lower bow, and being designed to be able to adjust the movement of the upper bow freely to a certain extent. In a conventional articulator of this type, the condyle portion is designed to be fixed by either a spring or a clamp screw, and also the indicator which is used, for example, to establish support at the eye point is secured by a clamp screw to the upper bow.

In the conventional articulator of the above-mentioned type, it should be noted that, because of its structure such that the condyle portion is to be fixed either by a spring or by a clamp screw as stated above, there have been the drawbacks that the workability at the time of moving the upper bow is poor, and moreover that the operation of the parts of the device is complicated, and further that the indicator can be used only for the indication of a single point such as the eye point, and also that this indicator obstructs the operation of the parts of the device.

SUMMARY OF THE INVENTION

It is, therefore, a primary object of the present invention to provide an improved Arcon-type semiadjustable dental articulator which has been worked out by paying attention to the above-mentioned drawbacks of the prior art, and which allows positive and accurate fixation of the condyle portion as well as its fixation at the centric occlusal position by a very simple operation.

Another object of the present invention is to provide an Arcon-type semi-adjustable dental articulator which is constructed so that the orbita indicator can be used for diversified purposes.

According to the present invention, the Arcon-type semi-adjustable dental articulator is designed so that the adjusting-and-fixing knob for the condylar box protrudes beyond the top surface of the condylar box, and also that the orbita indicator is detachably and slidably mounted on the incisal guide pin. Whereby, the adjusting-and-fixing operations of the adjustable guide plate can be accomplished in one-touch fashion, and the orbita indicator can be utilized not only as the means of indicating the eye point, the naso-auricular point and the occlusal plane, but also as the means of checking the plate for determining the occlusal plane and orientation, and further as the reference plate for use during the arrangement of artificial teeth.

These and other objects as well as the features and the advantages of the present invention will become apparent from the following detailed description of the preferred emodiment when taken in conjunction with the accompanying drawings.

BRIEF DESCRIPTION OF THE DRAWINGS

Like parts are assigned with like reference numerals throughout the drawings for the sake of simplicity.

DETAILED DESCRIPTION OF THE PREFERRED EMBODIMENT

The present invention will hereunder be described in further detail based on an embodiment illustrated herein.

Figure 1:
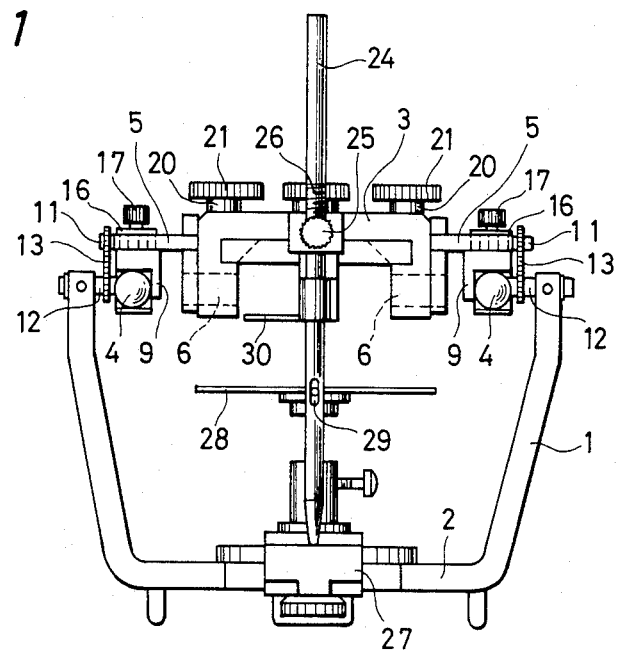
FIG. 1 is a front view of the semi-adjustable articulator according to the present invention.
Figure 2:
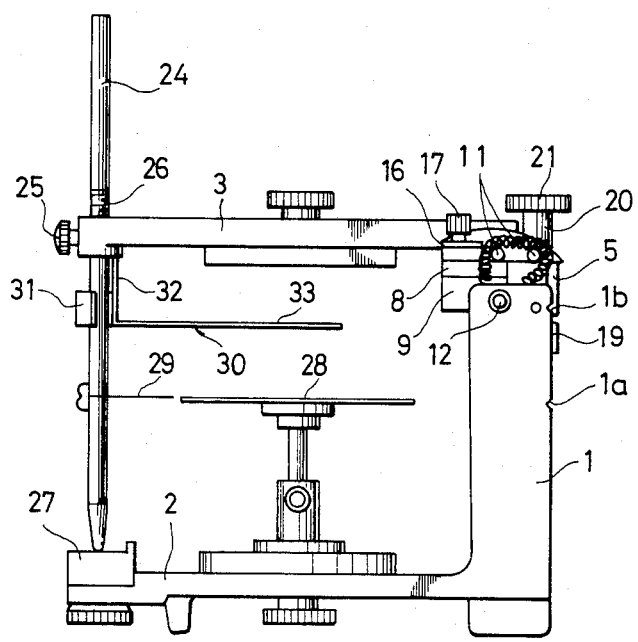
FIG. 2 is a side elevation of same.
Figure 3:
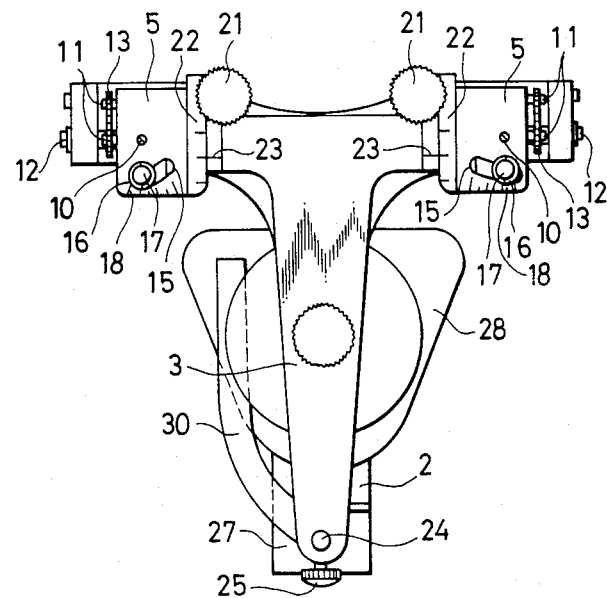
FIG. 3 is a plan view of same.
Figure 4:
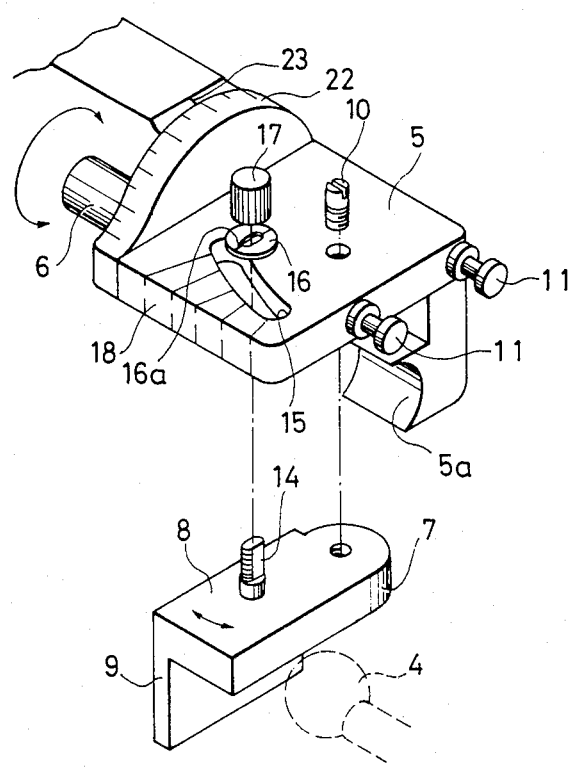
FIG. 4 is an enlarged exploded perspective view of the condyle portion.
Figure 5:
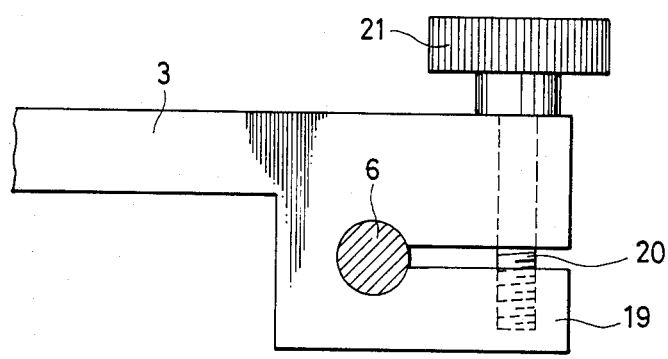
FIG. 5 is partial enlarged view of the portion where the condylar box is attached to the upper bow.
Figure 6:
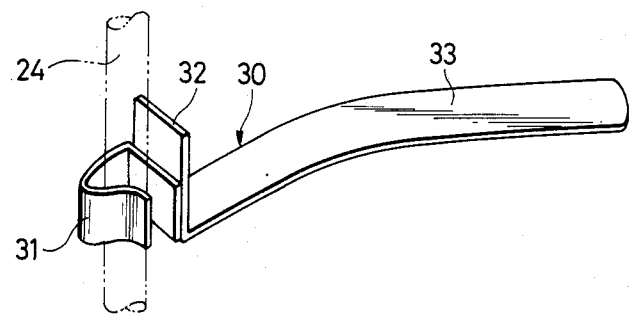
FIGS. 6 and 7 are enlarged perspective views, respectively, showing the mutually different manners of attachment of an orbita indicator to the incisal guide pin.
Figure 7:
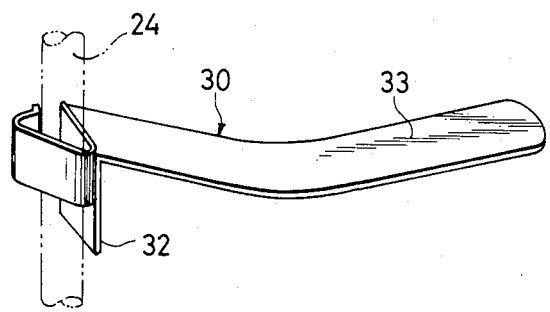

Reference numeral 1 represents a sustantially U-shaped articulator body, having, formed on a corner edge line between a back surface and an outer side surface of each of a pair of laterally spaced upright frame portions a notch 1a aligned with the occlusal plane in height and a notch 1b aligned with the ear point in height (see FIG. 2). Numeral 2 represents a lower bow framed integrally with the articulator body 1; 3 an upper bow pivotably mounted on the articulator body 1 in such a manner as will be described later; 4 a condyle ball secured to each lateral side of the articulator body 1; 5 a condylar box rotatably secured to each lateral side of the upper bow 3 by a rotatable axis 6. By coupling each condyle ball 4 to each condylar box 5, the semi-adjustable articulator is constructed. In each condylar box 5 is housed an adjustment guide plate 7 (FIG. 4) intended for guiding the direction of movement of the upper bow 3. This adjustment guide plate 7 is comprised of a sagittal condylar path inclination adjusting plate 8 and also of a balancing side lateral condylar path angle adjusting plate 9 arranged normal to the condylar path inclination adjusting plate 8. By rotatably attaching the sagittal condylar path inclination adjusting plate 8 to the bottom surface of the condylar box 5 by an axis 10, and by arranging two pins 11, 11 to protrude, side by side, from the external surface of the condylar box 5, and by securing the condylar box 5 to cover the condyle ball 4 from thereabove, and by bringing the condyle ball 4 into contact simultaneously with an arcuate surface formed on the condylar box 5 and with the sagittal condylar path inclination adjusting plate 8 and also with the balancing side lateral condylar path angle adjusting plate 9, and by coupling the condyle ball 4 to the condylar box 5 together by applying, under tension, an O-ring made of rubber or with a coil spring between the axial rod portion 12 of the condyle ball 4 and the pins 11, 11 protruding outwardly from the external side surface of the condylar box 5, there is constructed the articulator. The forward end portion of the screw rod 14 having a rectangular (or semicircular) cross section and extending outwardly from the upper surface of the sagittal condylar path inclination adjusting plate 8 is inserted through an arcuate slot 15 formed through the upper wall of the condylar box 5 concentrically with an axis 10, and an adjusting-and-fixing knob 17 is screwed onto said forward end portion of the screw rod 14 via a washer 16 which is made of a smoothly slidable material such as Derlin (trade name) and mounted around the threaded end portion of the screw rod and also provided with an indication marking 16a. Said knob 17 is loosened somewhat and is moved sideways together with the washer 16 along the slot 15 so as to bring the marking 16a which is scored on the surface of the washer 16 into alignment with a desired one of the balancing side lateral condylar path angle graduations 18 which, in turn, are formed to extend from the upper surface over to the forward lateral surface of the condylar box 5, and then the knob 17 is tightened to be fixed thereat. Whereby, the balancing side lateral condylar path angle of the balancing side lateral condylar path angle adjusting plate 9 is fixed at the desired angular position. Also, a knob 21 of a threaded rod 20 which is screwed into the forward end portion of a bifurcated portion 19 (FIG. 5) into which the rotatable axis 6 of the condylar box 5 has been inserted is nipped by two fingers of the user to turn and loosen the threaded rod 20 to thereby render the rotatable axis 6 freely rotatable. Along therewith, the condylar box 5 is held between two fingers of the user and is rotated to thereby bring a fixed marking 23 which is formed on the lateral end edge of the base portion of the upper bow 3 to be aligned with a desired one of the graduations 22 indicative of sagittal condylar path inclination degrees manifested on the arcuate surface which is integral with the condylar box 5, and thereafter the knob 21 is operated to tighten the threaded rod 20, whereby the sagittal condylar path inclination degree can be fixed at a desired angular position. It should be noted here that there is provided an arrangemet so that, when the sagittal condylar path inclination adjusting plates 8, 8 on both sides are fixed in such a way that the knobs 17, 17 are positioned at the outermost end (−10°) positions of the slots 15, 15 respectively, the upper bow 3 is able to perform only the pivotal movements without causing this upper bow 3 to detach from the lower bow 2 even in case the O-ring 13 is not provided, i.e. so as to insure that the fixation of the upper bow 3 at the centric occlusal position of the mandible can be effected without fail. Numeral 24 represents an incisal guide pin vertically and slidably inserted through the forward end portion of the upper bow 3 and being fixed to the upper bow 3 by tightening a threaded rod 25 provided with an operating knob. This incisal guide pin 24 is provided with graduations 26 for adjusting the position at which the incisal guide pin 24 is to be fixed by bringing the upper surface edge of the forward end portion of the upper bow 3 into alignment with a selected one of these graduations 26. Numeral 27 represents an incisal indicator plate; 28 an occlusal plane table and mounting jig; 29 an incisal indicator pin inserted through the incisal guide pin 24; and 30 an orbita indicator. The orbita indicator 30, as clearly shown in FIG. 6, is comprised of a base portion 31 made of a resilient member for detachably holding the incisal guide pin 24, an upwardly extending portion 32 extending along the incisal guide pin 24, and an elongated strip-like portion 33 intersecting said upwardly extending portion 32 at right angles. The orbita indicator 30 is constructed so that, in the state in which the incisal guide pin 24 is fixed at a position which is determined by bringing the upper surface edge of the forward end portion of the upper bow 3 into alignment with a reference graduation line among the graduations 26 formed on the incisal guide pin 24 and also in which the lower end of this guide pin 24 is brought into contact with the incisal guide plate 27, it is possible to obtain a coincidence between a plane containing the strip-like portion 33 and a plane containing the reference point of the condyle path portion when the upper surface of the upwardly extending portion 32 of the orbita indicator 30 is brought into contact with the bottom face of the forward end portion of the upper bow 3, and also possible to obtain a coincidence between the strip-like portion 33 and the occlusal plane table 28 by downwardly moving the position of the orbita indicator 30. It should be understood here that, because the orbita indicator 30 has its base portion made with a resilient material, not only its attachment and detachment to and from the incisal guide pin 24 are easy, but also the orbita indicator can be unfailingly held stationary at any position on the incisal guide pin 24. Accordingly, this oribta indicator 30 can be used by attaching, as shown in FIG. 7, in an upside down fashion relative to that shown in FIG. 6, and also it can be utilized to view the plate for determining the occlusal plane and orientation, in addition to the indication of the eye point and the indication of the naso-auricular line, and further to utilize it as a reference for arranging artificial teeth.

As described above, the dental articulator according to the present invention is of the construction that each knob 17 serves concurrently as an adjustment operating knob and as a fixing knob, and that graduations 18 are formed to extend on both the upper surface and the forward side surface of the condylar box 5, and that an indication marking 16a is formed on the washer 16 which moves integrally with the knob 17. Accordingly, by a very simplified manipulation from above the articulator, it is possible to quickly and accurately achieve an adjustment of both the sagittal condylar path inclination degree and the balancing side lateral condylar path angle, thus making it possible to form an artificial denture which adequately cooperates with the lower chin movements of any specific patient. Also, because the coupling of each condyle ball with its mating condylar box is performed by a resilient O-ring made of, for example, rubber or coil spring, not only it is possible to prevent the upper bow from its inadvertent up-lift, but also the parts can move very smoothly at the time of lateral movements as well as forward movements of the upper bow without causing separation of the latter from the lower bow, and besides the return of the upper bow to its centric occlusal position is ensured, and thus the denture-forming operation can be greatly facilitated with safety and with a good efficiency. Furthermore, according to the articulator of the present invention, the orbita indicator not only allows its attachment and detachment as well as its positioning to be effected in one-touch fashion, but also it can be utilized for diversified purposes. Thus, the manufacture of a denture can be performed all the more efficiently, thus providing a very great practical effect. Also, the articulator according to the present invention is so constructed that its positive fixation at the centric occlusal position can be done very easily, so that this articulator provides for a very high stability and safety during its handling, and it is possible to totally exclude the breakage of the constituent parts and the disorder of movable parts. Furthermore, the articulator of the present invention is such that its entire structure is simplified, so that the articulator can be provided at a relatively low cost. Moreover, the replacement of this constituent parts is easy, thus providing for a great convenience in its practical use.

What is claimed is:

1. A semi-adjustable dental articulator comprising an articulator body, an upper bow, a lower bow and an incisal guide pin adjustably attached to said upper bow, said upper bow being pivotably mounted to said articulator body by a pair of condyle balls attached to lateral sides of said articulator body and by condylar boxes rotatably attached to lateral sides of said upper bow, respectively, and adjustment guide plates each having an axis and rotatably attached to said condylar boxes, respectively, an improvement wherein:

said articulator further comprises:

a slot formed through an upper wall of each of said condylar boxes to have an arcuate shape concentric with the axis of the associated said adjustment guide plate;

balancing side lateral condylar path angle graduations formed on the upper wall of said condylar box adjacent to said slot; a screw rod extending outwardly from an upper surface of said adjustment guide plate and inserted through said slot; a washer fitted around said screw rod for movement only longitudinally of said screw rod and having, at an upper face, an indicator marking cooperating with said condylar path angle graduations; and a knob threadably mounted on said screw rod for functioning cooperatively with said washer, when loosened, as an adjusting member for said adjustment guide plate, and also functioning cooperatively with said washer, when tightened, as a clamping member for said adjustment guide plate, said articulator body is provided with a pair of laterally spaced upright frame portions each having a back surface and an outer side surface intersecting and forming an upright corner line, and said corner line having an indication notch aligned with an occlusion plane in height and another indication notch aligned with an ear point in height.

2. A semi-adjustable dental articulator according to claim 1, further comprising:

an orbita indicator detachably, semi-fixedly and slidably mounted on said incisal guide pin.

3. A semi-adjustable dental articulator according to claim 1, in which:

said washer is made of a material having a smoothly slidable surface.

4. A semi-adjustable dental articulator according to claim 2, in which:

said orbita indicator is made with a resilient material.

5. A semi-adjustable dental articulator according to claim 1, in which:

said knob is arranged so that, when it is clamped at the outermost end position of said slot, the upper bow is allowed to make only pivotal movements without being detached from the lower bow.

* * * * *